US010922504B2

(12) United States Patent
Mongrenier (10) Patent No.: US 10,922,504 B2
(45) Date of Patent: Feb. 16, 2021

(54) DEVICE FOR STORING ELEMENTS

(71) Applicant: BIOLOG-ID, Boulogne-Billancourt (FR)

(72) Inventor: Jean-Claude Mongrenier, Versailles (FR)

(73) Assignee: BIOLOG-ID, Boulogne-Billancourt (FR)

( * ) Notice: Subject to any disclaimer, the term of this patent is extended or adjusted under 35 U.S.C. 154(b) by 0 days.

(21) Appl. No.: 16/338,928

(22) PCT Filed: Oct. 24, 2016

(86) PCT No.: PCT/EP2016/075508
§ 371 (c)(1),
(2) Date: Apr. 2, 2019

(87) PCT Pub. No.: WO2017/153009
PCT Pub. Date: Sep. 14, 2017

(65) Prior Publication Data
US 2019/0220638 A1 Jul. 18, 2019

(30) Foreign Application Priority Data

Oct. 3, 2016 (FR) .................................... 16 59522

(51) Int. Cl.
*G06K 7/10* (2006.01)
*G07F 11/62* (2006.01)
(Continued)

(52) U.S. Cl.
CPC ....... *G06K 7/10366* (2013.01); *A61M 1/0286* (2014.02); *G06K 7/10356* (2013.01);
(Continued)

(58) Field of Classification Search
CPC .......... G06K 7/10366; G06K 7/10415; G06K 7/10356; A61G 12/001; A61M 1/0286;
(Continued)

(56) References Cited

U.S. PATENT DOCUMENTS 5,839,806 A   11/1998  Liu
7,537,295 B2   5/2009  Jackson
(Continued)

FOREIGN PATENT DOCUMENTS

CA   2545978 A1   11/2007
FR   2985590 A1    7/2013
(Continued)

OTHER PUBLICATIONS

International Search Report, dated Mar. 2, 2017, from corresponding PCT application No. PCT/EP2016/075508.
(Continued)

*Primary Examiner* — Suezu Ellis
(74) *Attorney, Agent, or Firm* — Nixon & Vanderhye (57) ABSTRACT

A device is provided for storing elements, each element including a first wireless communication unit. The device includes at least two drawer units each including: a drawer including a bottom defining at least one location for receiving an element; for each location, at least one second wireless communication unit including an antenna having a radiation-zone field, each antenna having a first state in which the antenna is activated and a second state in which the antenna is deactivated; and a data-processing unit able to control the activation and deactivation of the antenna of each second communication unit according to a control law.

10 Claims, 4 Drawing Sheets

(51) Int. Cl.
G07F 17/00 (2006.01)
G06Q 10/08 (2012.01)
G07G 1/00 (2006.01)
A61M 1/02 (2006.01)
G06K 19/07 (2006.01)

(52) U.S. Cl.
CPC ....... G06K 19/0723 (2013.01); G06Q 10/087 (2013.01); G07F 11/62 (2013.01); G07F 17/0092 (2013.01); G07G 1/009 (2013.01)

(58) Field of Classification Search
CPC ..... A61M 1/0245; A61M 1/025; G07F 11/62; G07F 17/0092; G06F 19/3462; G16H 20/13; G06Q 10/087; G06Q 10/0875; A61J 7/0084; A61J 2205/60
See application file for complete search history.

(56) References Cited

U.S. PATENT DOCUMENTS

| | | | | |
|---|---|---|---|---|
| 8,342,400 | B1 * | 1/2013 | Reese | G06F 19/3462 235/385 |
| 8,770,479 | B1 | 7/2014 | Shoenfeld | |
| 8,952,787 | B2 | 2/2015 | Hughes | |
| 9,260,243 | B2 | 2/2016 | Wilhelm | |
| 9,275,262 | B2 | 3/2016 | Mongrenier et al. | |
| 2001/0006368 | A1 | 7/2001 | Maloney | |
| 2002/0180588 | A1 | 12/2002 | Erickson et al. | |
| 2002/0190845 | A1 | 12/2002 | Moore | |
| 2003/0072676 | A1 | 4/2003 | Fletcher-Haynes et al. | |
| 2004/0046020 | A1 * | 3/2004 | Andreasson | A61J 1/14 235/385 |
| 2007/0272746 | A1 | 11/2007 | Ortiz et al. | |
| 2008/0231456 | A1 * | 9/2008 | Matityaho | H01Q 1/2216 340/572.7 |
| 2008/0264962 | A1 * | 10/2008 | Schifman | G07F 17/0092 221/1 |
| 2008/0316045 | A1 * | 12/2008 | Sriharto | G06F 19/3462 340/10.1 |
| 2009/0189767 | A1 | 7/2009 | Primm et al. | |
| 2009/0251293 | A1 * | 10/2009 | Azevedo | G07G 1/009 340/10.1 |
| 2011/0140831 | A1 | 6/2011 | Michael | |
| 2016/0113721 | A1 * | 4/2016 | Seremjian | G07F 17/0092 340/12.51 |
| 2016/0210481 | A1 | 7/2016 | Hussain et al. | |
| 2019/0247276 | A1 * | 8/2019 | Mongrenier | A61J 1/10 |
| 2019/0307936 | A1 * | 10/2019 | Rushing | B01F 15/065 |

FOREIGN PATENT DOCUMENTS

| | | |
|---|---|---|
| FR | 2988936 A1 | 10/2013 |
| JP | 2001-270608 A | 10/2001 |
| JP | 2006-219250 A | 8/2006 |
| JP | 2014-218377 A | 11/2014 |
| WO | 03/026724 A1 | 4/2003 |
| WO | 2010/004331 A1 | 1/2010 |

OTHER PUBLICATIONS

French Search Report, dated Feb. 20, 2017, from corresponding FR application No. 16 59522.
International Search Report, dated Apr. 19, 2017, from related PCT application No. PCT/EP2016/075498.
Amador et al., "Application of RFID technologies in the temperature mapping of the pineapple supply chain", Sensing and Instrumentation for Food Quality and Safety, 2009, pp. 26-33, vol. 3, Issue 1.
Borghino, "Intelligent blood bags optimize supplies and prevent dangerous mistakes", 2009, https://newatlas.com/author/dario-borghino/.
Gibson et al., "The Effect of Varying Temperatures on the Post-Transfusion Survival of Whole Blood During Depot Storage and After Transportation by Land and Air", Storage Temperature and Red Cell Preservation, 1946, pp. 747-755.
Hamill, "The 30-minute rule for reissuing blood: are we needlessly discarding units?", Transfusion, 1990, pp. 58-62, vol. 30, No. 1.
Fraunhofer-Gesellschaft, "Intelligent blood bags", Phys Org, 2009, https://phys.org/news/2009-12-intelligent-blood-bags.html.
Kim et al., "Smart Blood Bag Management System in a Hospital Environment", Personal Wireless Communications, PWC, 2006, Lecture Notes in Computer Science, pp. 506-517, vol. 4217.
Pick et al., "Temperature Changes in Donor Blood under Different Storage Conditions", Transfusion, 1971, pp. 213-215, vol. 11, No. 4.
Saxena et al., "The Risk of Bacterial Growth in Units of Blood that Have Warmed to More than 10° C.", American Journal of Clinical Pathology, 1990, pp. 80-83, vol. 94, No. 1.
Saxena et al., "A comprehensive assessment program to improve blood-administering practices using the Focus-PDCA model", Transfusion, 2004, pp. 1350-1356, vol. 44.
Shields, "Studies on Stored Whole Blood: IV. Effects of Temperature and Mechanical Agitation on Blood with and without Plasma", Transfusion, 1970, pp. 155-162, vol. 10, No. 4.

* cited by examiner

DEVICE FOR STORING ELEMENTS

BACKGROUND OF THE INVENTION

Field of the Invention

The present invention relates to a device for storing elements.

The present invention also relates to a facility comprising such a storage device.

The elements are for example pouches containing biological products such as blood products (pouches of primary blood, plasma, platelets, red blood cells, etc.) or cellular engineering products (stem cells, etc.), or drug pouches such as chemotherapy pouches.

Description of the Related Art

It is known to store such pouches in refrigerating structures made up of drawers in which the pouches are inserted. The pouches inserted in such structures generally comprise an identification tag, such as an RFID (radio frequency identification) tag, in which information relative to the corresponding pouch is stored. Furthermore, a reader, such as an RFID reader comprising at least one antenna, is arranged across from the provided location of the pouches of each drawer in order to read and update the information contained in the tags for said pouches.

However, interference may occur between the waves emitted by the antenna of each RFID reader, which makes it difficult to read information stored on the identification tags, and therefore to check the state of the corresponding elements.

As a result, there is a need for a device for storing elements making it possible to check the state of said elements reliably.

BRIEF SUMMARY OF THE INVENTION

To that end, the invention relates to a device for storing elements, each element comprising a first wireless communication unit in which information relative to said element is stored, the device comprising at least two drawer units assembled on one another to form a vertical stack, each drawer unit comprising:
  a support comprising a housing,
  a drawer positioned in the housing of the support and able to slide relative to the support, the drawer comprising a bottom defining at least one location for receiving an element,
  for each location, at least one second wireless communication unit able to emit radio waves, each second communication unit being arranged across from the corresponding location, each second communication unit being suitable for communicating with the set of first communication units, each second communication unit comprising at least one antenna having a radiation-zone field, the radiation-zone field of each antenna covering at least:
    the location across from the second communication unit of said antenna, and
    at least one location adjacent to said location across from the second communication unit of said antenna,
  each antenna further comprising a first state in which said antenna is activated and a second state in which said antenna is deactivated,
  a data processing unit connected to each second communication unit, the processing unit being able to command the activation and deactivation of the antenna of each second communication unit according to a control law to determine whether the location across from the second communication unit of said antenna is occupied by an element and, if applicable, the information relative to said element.

According to specific embodiments, the device comprises one or more of the following features, considered alone or according to any technically possible combinations:
  each second communication unit corresponding to a location, the control law is chosen so as to command, in parallel, the activation of the antenna of said second communication unit and the deactivation of the antenna (s) adjacent to said antenna, such that the antenna of each second communication unit is activated at time intervals different from the time intervals of the antennas adjacent to said antenna;
  the processing unit is able to determine the location to which the information collected by each antenna corresponds based on information communicated by the set of antennas;
  the bottom of each drawer is made from a material able to be traversed by radio waves emitted by the second communication units;
  each second communication unit is arranged above the corresponding location;
  each second communication unit is arranged below the bottom of the drawer of the corresponding location;
  each drawer unit comprises a plate positioned below the bottom of the drawer of each drawer unit and below the second communications units corresponding to the locations at the bottom of the drawer of said drawer unit, each plate being able to prevent the passage of radio waves emitted by all of the second communication units;
  each first communication unit is a radio identification tag and each second communication unit is a radio identification reader.

The invention also relates to a facility, comprising:
  an enclosure comprising an inner compartment, and
  a device as described above, the device being arranged in the inner compartment of the enclosure.

According to specific embodiments, the facility comprises one or more of the following features, considered alone or according to any technically possible combinations:
  the elements being platelet containers, the enclosure being a platelet agitator.

BRIEF DESCRIPTION OF THE DRAWINGS

Other features and advantages of the invention will appear upon reading the following description of embodiments of the invention, solely as an example and done in reference to the drawings, which are.

DETAILED DESCRIPTION OF THE PREFERRED EMBODIMENTS

Figure 1:
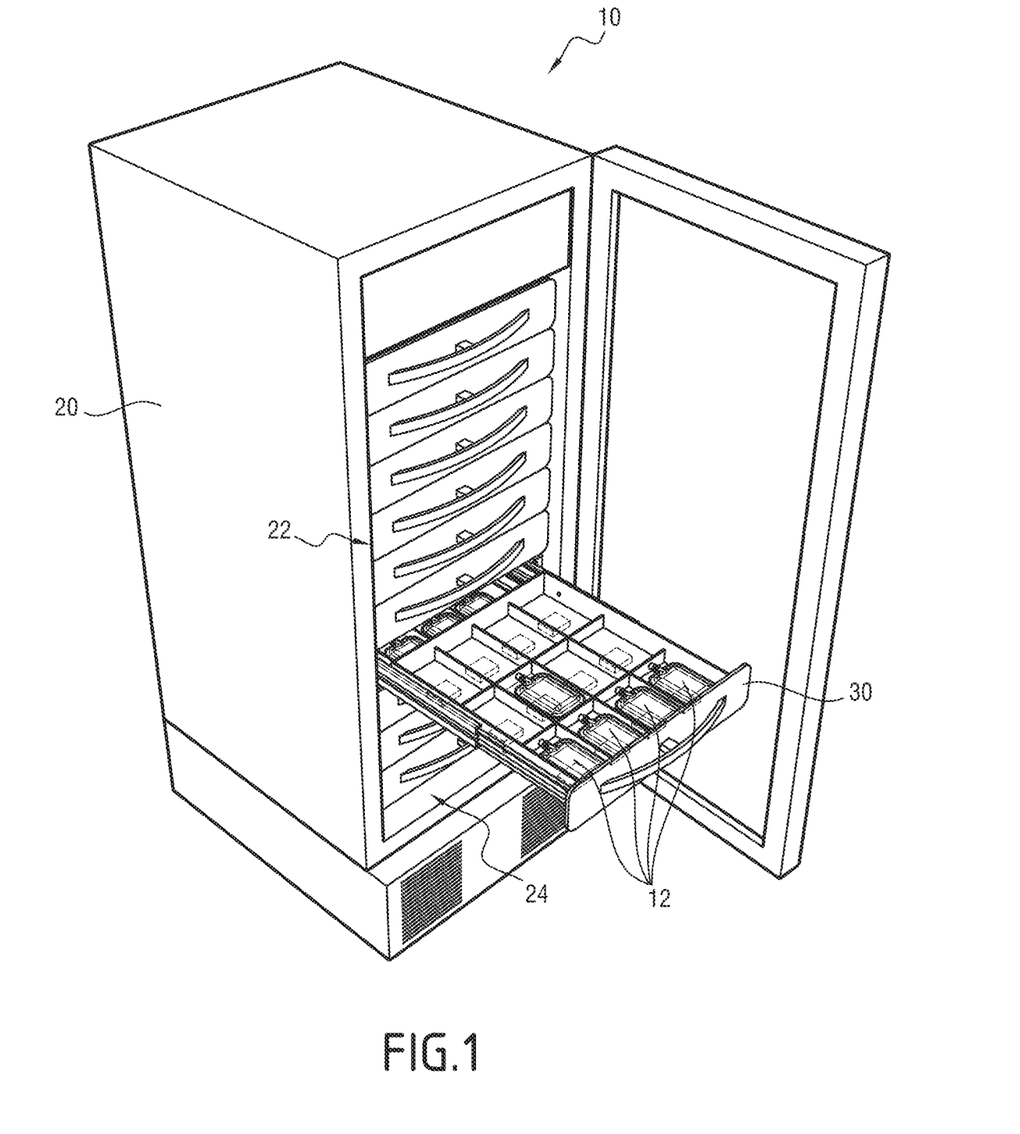
FIG. 1, a schematic perspective illustration of a facility comprising a storage device, FIG. 2, a schematic perspective illustration of the storage device of FIG. 1, FIG. 3, a schematic illustration of several drawer units of the storage device of FIG. 1, and FIG. 4, a schematic illustration of an element intended to be stored in the device of FIG. 1.

A facility 10 for storing elements 12 is illustrated in FIG. 1.

Figure 2:
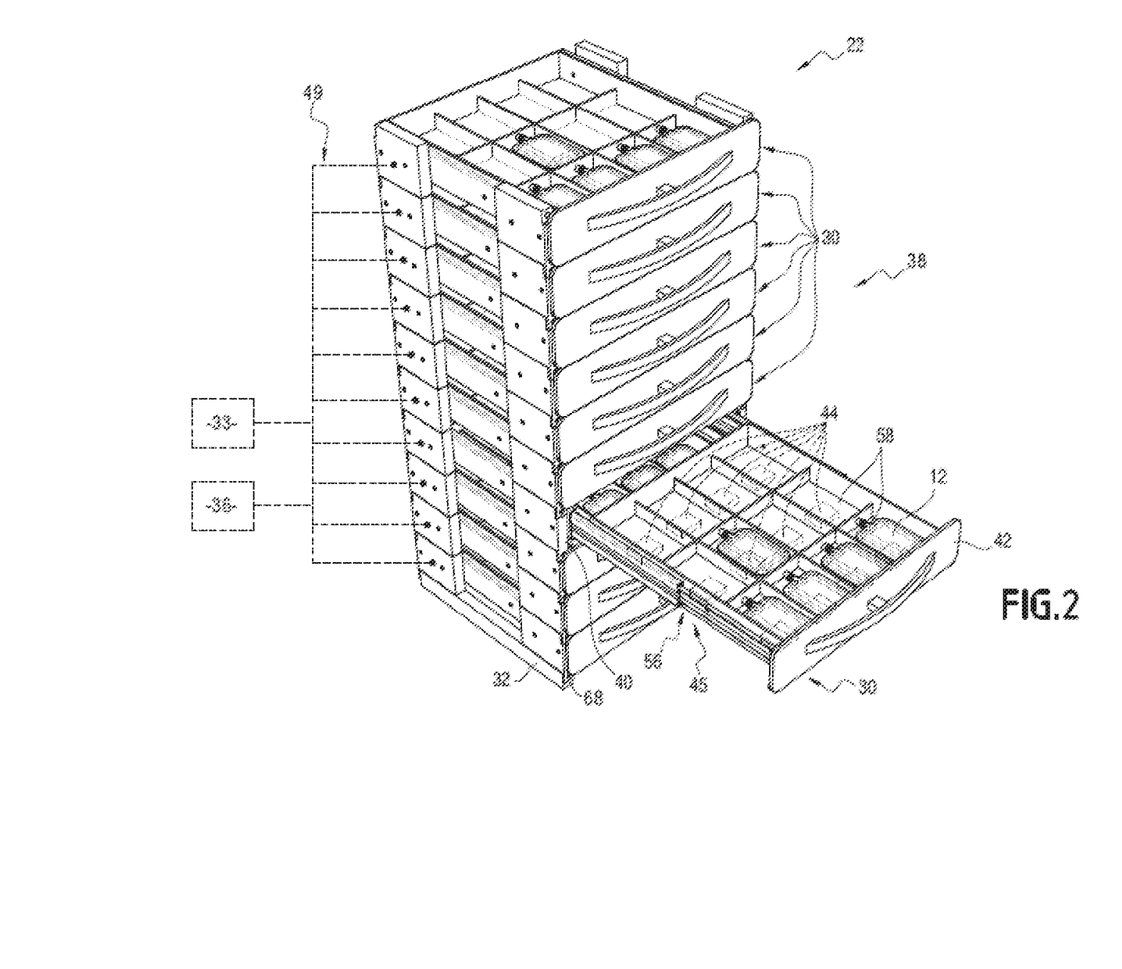

The elements 12 are for example containers (shown in FIG. 2). Generally, a container refers to any type of pouch intended to contain products whose use is subject to strict storage constraints.

More particularly, the elements 12 are for example pouches containing biological products such as blood products (pouches of primary blood, plasma, platelets, red blood cells, etc.) or cellular engineering products (human or animal cells, in particular human or animal stem cells, products from human or animal cells).

Alternatively, the elements 12 are drug pouches or therapeutic preparation pouches containing one or more active ingredients or medicaments, such as chemotherapy pouches (generally containing a solute and one or more chemotherapy active ingredients).

More generally, the elements 12 are able to contain any product designed to be infused in a human or animal.

Figure 4:
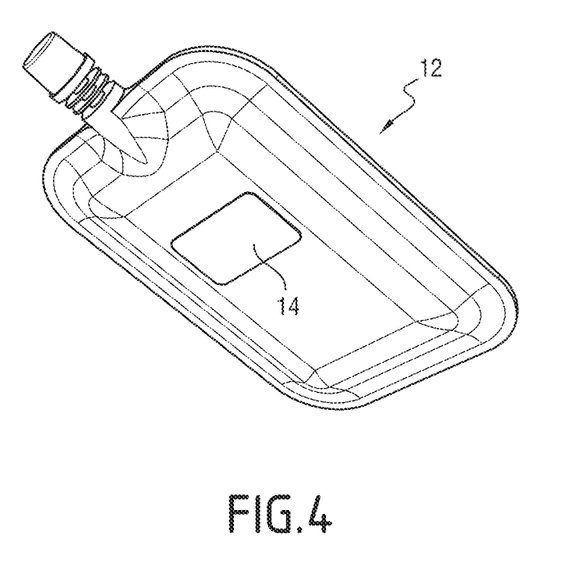

As shown in FIG. 4, each element 12 comprises a first wireless communication unit 14. Each first communication unit 14 is for example a tag, such as an adhesive tag affixed on an outer face of the element 12.

In general, each first communication unit 14 comprises at least an antenna, a memory and, optionally, a microprocessor.

The antenna of each first communication unit 14 is for example a radiofrequency antenna.

The memory of each first communication unit 14 comprises information relative to the corresponding element 12.

Such information is for example: a unique identifier of the element 12, the storage date of the element 12, the expiration date of the element 12, the date on which the first communication unit 14 of the element 12 communicated information for the last time, the donation number relative to the contents of the element 12, the product code of the contents of the element 12, the rhesus group of the contents of the element 12, the blood phenotype of the contents of the element 12, the identity of the patient from whom the contents of the element 12 originated, the name of the patient from whom the contents of the element 12 originated, the volume of the contents of the element 12, the donation center (including the address) where the contents of the element 12 were obtained, the process underway on the element 12 and the anticoagulant type of the contents of the element 12. In the case of chemotherapy, such information further comprises the production date, the product type, the excipient type, the identity of the prescribing doctor, the identity of the pharmacist, the identity of the manufacturer, the release date and the status (released, delivered, etc.).

The facility 10 comprises an enclosure 20 and a storage device 22.

The enclosure 20 comprises an inner compartment 24 receiving the storage device 22.

The enclosure 20 is for example a refrigerating enclosure or a freezer. When the refrigerating enclosure is a refrigerator, the temperature of the enclosure is comprised between 0 degrees Celsius (° C.) and 5°, preferably equal to 4°. When the refrigerating enclosure is a freezer, the temperature of the enclosure is comprised between −35° C. and −196° C., preferably equal to −40° C.

Alternatively, the enclosure 20 is a platelet agitator. The enclosure 20 is then preferably integrated into an incubator having a temperature preferably equal to 24° C.

Hereinafter, relative positions are defined with respect to a common usage direction of the enclosure 20 for which a bottom is defined, generally resting on the ground, and a top opposite the bottom. These relative positions are in particular shown by terms such as "below" or "above".

The device 22 comprises a plurality of drawer units 30 and a base 32. As shown in FIG. 2, the device 22 further comprises a processing unit 33.

Figure 3:
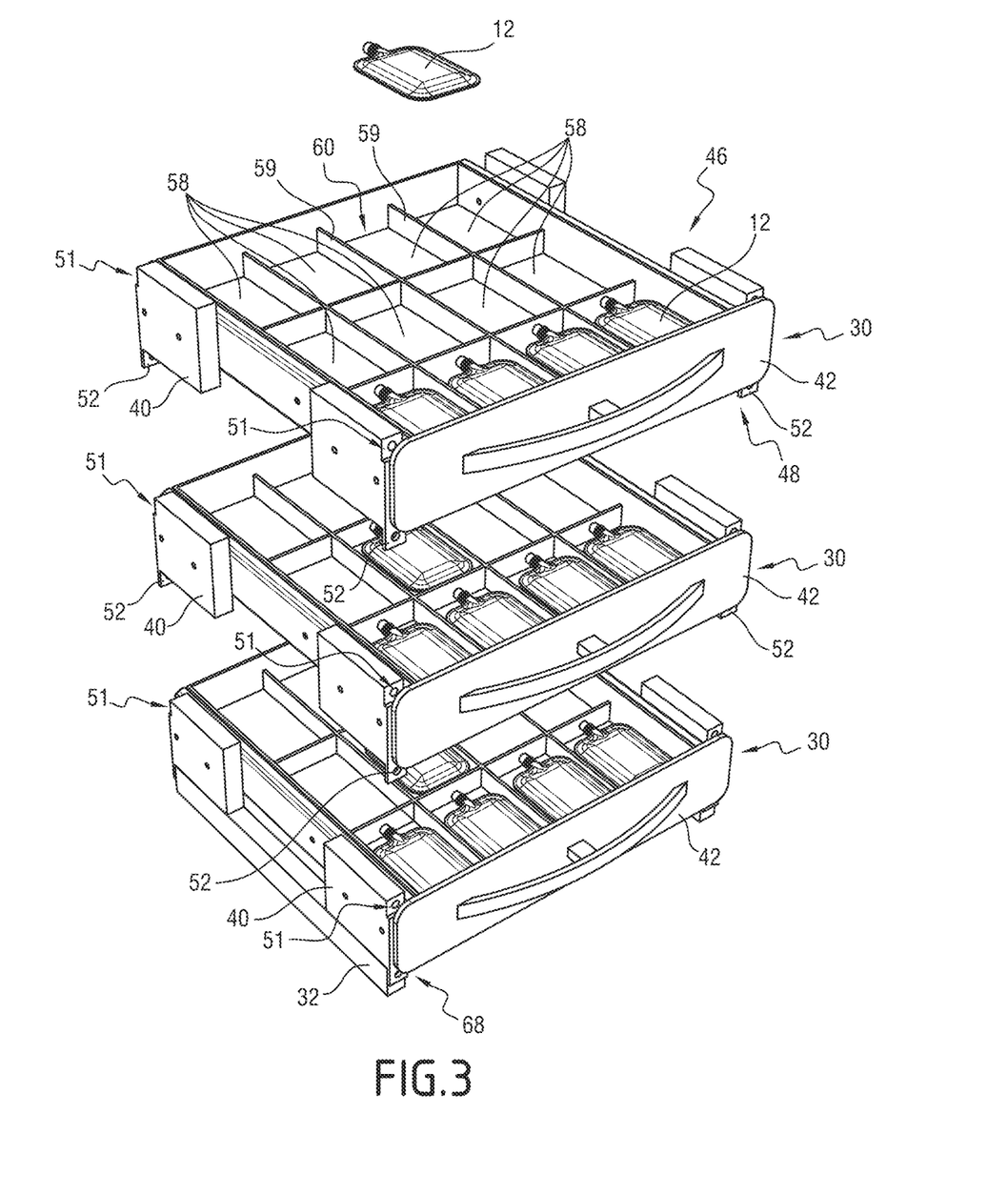

As described later, the drawer units 30 are stacked on one another to form a vertical stack 38 of drawer units 30. FIGS. 1 to 3 illustrate one example of a stack of ten drawer units 30.

Each drawer unit 30 comprises a support 40, a drawer 42 and at least one second communication unit 44, shown in FIG. 2.

The support 40 comprises a housing 45, an upper end 46, a lower end 48 (shown in FIG. 3) and connections 49 (shown in FIG. 2).

Each housing 45 is able to receive the corresponding drawer 42.

The upper end 46 of each drawer unit 30, shown in FIG. 3, comprises at least a first assembly member 51. The first assembly members 51 are for example female assembly members.

The lower end 48 of each drawer unit 30, shown in FIG. 3, comprises at least a second assembly member 52, complementary to the first assembly members 51. The second assembly members 52 are for example male assembly members.

In the example illustrated in FIG. 3, the first assembly members 51 are slots and the second assembly members 52 are ribs complementary to the slots.

Thus, each drawer unit 30 is assembled to at least one other drawer unit 30 of the stack 38 by the first assembly member(s) 51 of said drawer unit 30 and/or by the second assembly member(s) 52 of said drawer unit 30.

The connections 49 are for example electrical connections.

In the embodiment illustrated in FIGS. 1 to 3, the connections 49 of each drawer unit 30 are connected on the one hand to the second communication units 44 of said drawer unit 30, and on the other hand the second communication units 44 of the other drawer units 30. Furthermore, the connections 49 are connected to the processing unit 33.

Each drawer 42 is positioned in the housing 45 of the support 40. Each housing 42 is able to slide relative to the corresponding support 40.

Each drawer 42 comprises a bottom 56 defining at least one location 58 for receiving an element 12.

The bottom 56 of each drawer 42 is made from a material able to be traversed by radio waves emitted by the second communication unit 44 of the drawer unit 30 of said drawer 42.

The material of the bottom 56 of each drawer 42 is for example plastic.

In the embodiment illustrated in FIGS. 1 to 3, the bottom 56 of each drawer 42 defines twelve locations 58 for receiving elements 12.

Each location 58 is for example defined by rims 59 forming a pigeonhole 60.

In the embodiment illustrated in FIGS. 1 to 3, each drawer unit 30 comprises as many second communication units 44 as locations 58.

In the embodiment illustrated in FIGS. 1 to 3, each second communication unit 44 is arranged below the bottom 56 of the drawer 42 across from the corresponding location 58, so as to allow the communication between said second communication unit 44 and the first communication unit 14 of an element 12 received in said location 58.

The expression "across from" refers to the fact that each second communication unit 44 is arranged facing the space defined by the location 58. In other words, the projection of the location 58 in the plane of the second communication unit 44 is combined with the second communication unit 44.

Alternatively, at least one second communication unit 44 is arranged above the corresponding location 58.

Each second communication unit 44 is able to communicate, if applicable, with the first communication unit 14 of the element 12 received in said location 58 to obtain information relative to the element 12.

Each second communication unit 44 is able to emit radio waves. Each second communication unit 44 is suitable for communicating with the set of first communication units 14.

In one example embodiment, the first communication units 14 are RFID tags and the second communication units 44 are RFID readers.

More generally, each second communication unit 44 comprises at least an antenna, a memory, and optionally, a microprocessor.

The radiation-zone field of each antenna covers at least:
the location 58 across from the second communication unit 44 of said antenna, and
at least one location 58 adjacent to said location 58 across from the second communication unit said antenna.

More specifically, the radiation-zone field of each antenna covers the locations 58 near the antenna based on the intensity and form of the magnetic field of the antenna.

Each antenna further comprises two states: a first state in which said antenna is activated, and a second state in which the antenna is deactivated. An activated antenna is an antenna able to resonate with a predetermined impedance and a predetermined frequency. The predetermined impedance is for example equal to 50 ohms (Ω) and the predetermined frequency is for example equal to 13.56 Megahertz (MHz). Thus, the resonance frequency of an activated antenna is close to the working frequency of said antenna. A deactivated antenna is an antenna that is not capable of resonating at the predetermined frequency. The deactivation of an antenna is for example done by opening the loop of said antenna or detuning the antenna such that the impedance of said antenna at the resonance frequency has a real (or resistive) component much lower than the imaginary (or reactive) component of said antenna.

In the embodiment illustrated in FIGS. 1 to 3, each second communication unit 44 is secured to the drawer 42 of the corresponding drawer unit 30. More specifically, each second communication unit 44 is fastened below the bottom 56 of the drawer 42 of the corresponding location 58.

In one alternative, each second communication unit 44 is secured to the support 40 of the corresponding drawer unit 30. Each drawer unit 30 further comprises a satellite. The satellite is a case that contains the second communication unit 44. The satellite is fastened to the support 40 of said drawer unit 30 directly below the drawer 42 of said drawer unit 30. When the drawer 42 is closed, said second communication unit 44 is across from the corresponding location 58 and is therefore, if applicable, capable of communicating with a first communication unit 14 positioned in the corresponding location 58. When the drawer 42 is open, said second communication unit 44 is not moved with the drawer 42, and consequently is not capable of communicating with a first communication unit 14 positioned in the corresponding location 58.

Optionally, each drawer unit 30 also comprises a plate.

Each plate is able to prevent radio waves emitted by all second communication units 44 from passing. Each plate is for example made from metal.

Each plate is positioned below the bottom 56 of the drawer 42 of each drawer unit 30 and below the second communications units 44 corresponding to the locations 58 at the bottom 56 of the drawer 42 of said drawer unit 30. Thus, each second communication unit 44 is suitable for communicating only with the first communication units 14 positioned above said second communication unit 44.

The base 32 is assembled with the lowest drawer unit 30 of the stack 38 of drawer units 30. To that end, the base 32 comprises an upper end comprising at least a third assembly member 68. Each third assembly member 68 is identical to the first assembly members 51. The second assembly member(s) 52 of the last drawer unit 30 of the stack 38 are assembled with the third assembly member(s) 68 of the base 32, which makes it possible to close the stack 38.

The processing unit 33 is connected to each second communication unit 44.

The processing unit 33 is able to process the information from the two communication units 44. In particular, the data processing unit 33 is able to command the activation and deactivation of the antenna of each second communication unit 44 according to a control law to determine whether the location across from the second communication unit 44 of said antenna is occupied by an element 12 and, if applicable, the information relative to said element 12.

More specifically, for each second communication unit 44 corresponding to a location 58, the control law is chosen so as to command, in parallel, the activation of the antenna of said second communication unit 44 and the deactivation of the antenna(s) adjacent to or across from said antenna, or more generally near said antenna, such that the antenna of each second communication unit 44 is activated at time intervals different from the time intervals of the antennas adjacent to said antenna.

The control law is suitable for allowing each second communication unit 44 to communicate with any first communication unit 14 positioned in the corresponding location 58, without interference with the waves emitted by the antennas of the second communication units 44 adjacent to said second communication unit 44. Thus, the antenna of each second communication unit 44 is activated and deactivated at time intervals established based on the second communication units 44 adjacent to said second communication unit 44.

The control law depends on the position of the antennas of each second communication unit 44 and the radiation-zone field of said antennas.

For example, it is assumed that the radiation-zone field of each antenna covers the location 58 across from the antenna and the locations 58 adjacent (sideways, above, below and diagonally) to said location 58. To ensure the interference of a given second communication unit 44 without interference, the control law commands the deactivation, for a defined duration, of the antennas of the second communication units 44 across from the locations adjacent to said second communication unit 44 and the activation of the antenna of said second communication unit 44. The same command is repeated at different time intervals for the other second communication units 44.

In another example, the control law commands the deactivation of the set of antennas and the activation, one by one, of each antenna at different time intervals.

In still another example, the control law commands the activation of only one antenna per drawer unit 30 by choosing antennas that are not across from one another and the deactivation of all of the other antennas.

The processing unit 33 is further able to determine the location to which the information collected by each antenna corresponds based on information communicated by the set of antennas.

Indeed, inasmuch as the radiation-zone field of each antenna covers, aside from the location 58 corresponding to said antenna, at least one other adjacent location 58, the processing unit is configured to determine the origin of the information collected by each antenna.

For example, it is assumed that the antennas are arranged below the drawers 42 and that the radiation-zone field of each antenna covers the location 58 across from the antenna (therefore above the antenna) and the location 58 adjacent to the antenna and situated in the drawer 42 at the bottom of the antenna (therefore below the antenna). The processing unit 33 is able to compare the information collected by the adjacent antennas and to thereby determine the information corresponding to the location across from each antenna. In this example, let us assume that a first antenna across from a first location 58 detects a first signal A and a second signal B and that a second adjacent antenna directly below the first antenna detects the second signal B and a third signal C. The processing unit 33 determines that the second signal B detected by each of the first and second antennas comes from a first communication unit 44 of an element 12 positioned in the first location. The processing unit 33 further determines that the first signal A is coming from a first communication unit 44 of an element 12 positioned in the location 58 adjacent to and directly above the first location 58. The processing unit 33 also determines that the third signal C is coming from a first communication unit 44 of an element 12 positioned in the location 58 adjacent to and directly below the first location 58.

In general, the control law is chosen so that the processing unit 33 reliably determines the location(s) 58 to which the information collected by each antenna corresponds.

As an optional addition, the processing unit 33 is able to account for the strength of the signal, called RSSI (return signal strength intensity), emanating from each antenna. In practice, the closer an antenna is to a first communication unit, the better the RSSI is, i.e., the RSSI is high. For example, for a RSSI from 0 to 7: "7" means that the antenna is as close as possible to the first communication unit and "0" means that the antenna is not detecting any signal.

For example, for a device 22 comprising six drawer units 30, five antennas and one first communication unit 14 positioned in the third drawer unit 30, the RSSI could be {3, 6, 7, 2, 0}.

For example, to find the first communication unit 14, the processing unit 33 is able to consider that said first communication unit 14 is between the two antennas having the strongest RSSI. Alternatively, the processing unit 33 is able to determine said first communication unit 14 by performing weighted mean or k-mean calculations on the obtained RSSIs.

Lastly, the processing unit 33 is able to determine the occupation of each location 58, and if applicable, from said information, a state of the element 12 positioned in said location 58.

There are for example two determined states: a "valid" state and an "invalid" state. An element 12 is considered to be "valid" when the information relative to the element 12 is according to specifications and is considered "invalid" otherwise.

Thus, the processing unit 33 has an instantaneous image of the storage device 22, namely which element 12 is in which location 58 and the information relative to each of said elements 12. The processing unit 33 also comprises a log of the entry and exit dates of each element 12 relative to the device 22.

Optionally, the processing unit 33 is able to sequence, if applicable, the update, by the second communication units 44, of the information contained in the first communication units 14.

Optionally, the processing unit 33 is able to generate an alarm based on the occupation of each location 58 and, if applicable, the state of the element 12 corresponding to said location 58. For example, if the processing unit 33 determines that a same location 58 comprises more than one element 12, the processing unit 33 generates an alarm.

The operation of the device 22 integrated into the facility 10 will now be described.

The processing unit 33 commands the activation and deactivation of the antenna of each second communication unit 44 according to the control law. This allows the antenna of each second communication unit 44 to collect, if applicable, information relative to the elements 12 of the corresponding locations 58. The processing unit 33 determines, from said information, the locations 58 occupied by the elements 12, and if applicable, a state of the elements 12. Depending on the case, the processing unit 33 activates, or does not activate, an alarm.

Thus, the device 22 allows reliable checking of the state of the elements 12 stored in the device 22, as well as the occupancy rate of the locations 58 of the drawer units 30.

In particular, the activation and deactivation of the antennas based on the control law makes it possible to reduce the interference between signals, which improves reading of the information stored on the first communication units 14.

Furthermore, the specific positioning of the readers below the corresponding drawer makes it possible to obtain a smaller bulk.

The device 22 is therefore a device for storing elements making it possible to check the status of elements 12 reliably without cluttering the storage area.

Furthermore, it is easy to assemble and disassemble the drawer units 30 of the device 22. Such configurability of the device 22 makes it possible to adapt the device 22 to a large number of facilities 10, by modifying the number of drawer units 30 of the stack 38.

Furthermore, a stack of drawer units is much lighter and more compact than a plurality of drawers, and therefore easier to manipulate and install.

Additionally, from a production standpoint, thousands of identical drawer units 30 are manufactured, rather than dozens of cabinets with different formats. This makes it possible to achieve economies of scale, simplify inventory management, and simplify maintenance.

Furthermore, the device 22 is adaptable to a facility 10 not already having RFID technology.

Additionally, the reduced bulk makes it possible to consider configurations in which the facility 10 contains a larger number of elements 12.

Moreover, the facility 10 and/or the device 22 are easy to produce.

Lastly, in an alternative according to which each drawer unit 30 comprises a satellite, the satellite is in a single unit and is therefore easy to replace in case of failure.

The invention claimed is:

1. A device configured to store a plurality of elements, each element including a first wireless communication unit in which information relative to said element is stored such that a set of first wireless communication units is provided for the plurality of elements, the device comprising:

at least two drawer units assembled on one another to form a vertical stack, each drawer unit comprising:
a support comprising a housing,
a drawer positioned in the housing of the support and configured to slide relative to the support, the drawer comprising a bottom defining at least two locations each configured to receive one of the elements,
for each of the at least two locations, at least one second wireless communication unit configured to emit radio waves, each second communication unit being disposed facing the respective location, each second communication unit being configured to communicate with the set of first communication units, each second communication unit comprising at least one antenna having a radiation-zone field, the radiation-zone field of each antenna covering at least:
the location facing the respective second communication unit of said antenna, and
at least one other location of the at least two locations adjacent to said location facing the respective second communication unit of said antenna,
each antenna having a first state in which said antenna is activated and a second state in which said antenna is deactivated, and
a data processor connected to each second communication unit, the data processor being configured to command activation and deactivation of the antenna of each of the second communication units according to a control law to determine whether the location facing the respective second communication unit of said antenna is occupied by one of the elements and, when it is applicable, the information relative to said element.

2. The device according to claim 1, wherein each second communication unit corresponds to one of the locations,
the control law is chosen to command, in parallel, the activation of the antenna of said second communication unit and the deactivation of one or more of the antennas adjacent to said antenna, such that the antenna of each second communication unit is activated at time intervals different from the time intervals of the antennas adjacent to said antenna.

3. The device according to claim 2, wherein the data processor is configured to determine the location to which the information collected by each antenna corresponds based on information communicated by the antennas.

4. The storage device according to claim 1, wherein the bottom of each drawer is made from a material configured to be traversed by radio waves emitted by the second communication units.

5. The device according to claim 1, wherein each second communication unit is disposed above the respective location.

6. The device according to claim 1, wherein each second communication unit is disposed below the bottom of the drawer of the corresponding location.

7. The storage device according to claim 6, wherein each drawer unit further comprises a plate positioned below the bottom of the drawer of the respective drawer unit and below the second communication units corresponding to the locations at the bottom of the drawer of said drawer unit, each plate being configured to prevent the passage of radio waves emitted by all of the second communication units.

8. The device according to claim 1, wherein each first communication unit is a radio identification tag, and each second communication unit is a radio identification reader.

9. A facility, comprising:
an enclosure comprising an inner compartment, and
the device according to claim 1, the device being disposed in the inner compartment of the enclosure.

10. The facility according to claim 9, wherein the elements are platelet containers, the enclosure being a platelet agitator.

* * * * *